United States Patent
Makarenkova et al.

(10) Patent No.: US 11,877,906 B2
(45) Date of Patent: Jan. 23, 2024

(54) DENTAL ARCH WIDTH MEASUREMENT TOOL

(71) Applicant: Align Technology, Inc., San Jose, CA (US)

(72) Inventors: Svetlana Makarenkova, Moscow (RU); Ilya Agafonov, Reutov (RU); Boris Likhtman, Pushkino (RU); Pavel Sokolov, Moscow (RU); Vladimir Fedorov, Moscow (RU)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 17/962,205

(22) Filed: Oct. 7, 2022

(65) Prior Publication Data

US 2023/0033851 A1  Feb. 2, 2023

Related U.S. Application Data

(63) Continuation of application No. 16/457,731, filed on Jun. 28, 2019, now Pat. No. 11,464,604.

(60) Provisional application No. 62/692,138, filed on Jun. 29, 2018.

(51) Int. Cl.
| | |
|---|---|
| *A61C 7/00* | (2006.01) |
| *A61B 5/107* | (2006.01) |
| *A61C 9/00* | (2006.01) |
| *G16H 30/20* | (2018.01) |
| *G06T 19/20* | (2011.01) |

(52) U.S. Cl.
CPC ............ *A61C 7/002* (2013.01); *A61B 5/1076* (2013.01); *A61B 5/1079* (2013.01); *A61C 9/0053* (2013.01); *G06T 19/20* (2013.01); *G16H 30/20* (2018.01); *A61C 2007/004* (2013.01); *G06T 2219/004* (2013.01); *G06T 2219/2004* (2013.01); *G06T 2219/2016* (2013.01)

(58) Field of Classification Search
CPC ..... A61B 5/1076; A61B 5/1079; A61C 7/002; A61C 9/0053; A61C 2007/004; G16H 30/20; G06T 19/20; G06T 2219/004; G06T 2219/2004; G06T 2219/2016
See application file for complete search history.

(56) References Cited

U.S. PATENT DOCUMENTS

| | | | |
|---|---|---|---|
| 2003/0163291 A1* | 8/2003 | Jordan | A61C 7/00 703/1 |
| 2007/0168152 A1* | 7/2007 | Matov | G16H 30/20 702/155 |

(Continued)

*Primary Examiner* — Kee M Tung
*Assistant Examiner* — Jed-Justin Imperial
(74) *Attorney, Agent, or Firm* — Shay Glenn LLP

(57) ABSTRACT

Systems and methods for rapidly and reliably determining an arch with of a patient's dental arch. A first portion of a 3D model of a patient's dentition is identified that corresponds to a first target tooth, the first portion of the 3D model is associated with one or more attributes of the first target tooth. A second portion of the 3D model is identified that corresponds to a second target tooth opposing the first target tooth. The second portion is associated with one or more attributes of the second target tooth. The arch width is automatically measured based on the attributes of the first and second target teeth. A graphic representing the arch width is overlayed on the patient's dentition.

14 Claims, 11 Drawing Sheets

(56) References Cited

U.S. PATENT DOCUMENTS

2008/0050692 A1* 2/2008 Hilliard .................. A61C 7/08
433/24
2016/0175068 A1* 6/2016 Cai ....................... A61C 7/002
700/98

* cited by examiner

DENTAL ARCH WIDTH MEASUREMENT TOOL

CROSS REFERENCE TO RELATED APPLICATIONS

This patent application is a continuation of U.S. patent application Ser. No. 16/457,731, filed Jun. 28, 2019, titled "DENTAL ARCH WIDTH MEASUREMENT TOOL," now U.S. Pat. No. 11,464,604, which claims priority to U.S. Provisional Patent Application No. 62/692,138, filed on Jun. 29, 2018, titled "DENTAL ARCH WIDTH MEASUREMENT TOOL," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Dental treatments (e.g. orthodontic, restorative, etc.) using a series of patient-removable appliances (e.g., "aligners") can be useful for treating various conditions, such as malocclusions. Treatment planning is typically performed in conjunction with the dental professional (e.g., dentist, orthodontist, dental technician, etc.), by generating a model of the patient's teeth in a final configuration and then breaking the treatment plan into a number of intermediate stages (steps) corresponding to individual appliances that are worn sequentially. This process may be interactive, adjusting the staging and in some cases the final target position, based on constraints on the movement of the teeth and the dental professional's preferences. Once the final treatment plan is finalized, the series of appliances may be manufactured to implement the treatment plan.

This treatment planning process may include many manual steps that are complex and may require a high level of knowledge of orthodontic norms. Further, because the steps are performed in series, the process may require a substantial amount of time. Manual steps may include preparation of the model for digital planning, reviewing and modifying proposed treatment plans (including staging) and aligner features placement (which includes features placed either on a tooth or on an aligner itself). These steps may be performed before providing an initial treatment plan to a dental professional, who may then modify the plan further and send it back for additional processing to adjust the treatment plan, repeating (iterating) this process until a final treatment plan is completed and then provided to the patient. During the treatment planning process, the dental professional may review the current state of the patient's teeth, each iterative stage of treatment, and the final treatment stage.

Some cases, such as those involving pediatric or teen patients and/or patients with narrow jaws, may call for arch and/or palatal expansion, e.g., the application of forces to expand a patient's arch and/or palate. Such procedures may be performed using a variety of devices (fixed and/or removable palatal expanders, arch expanders, etc.), before closure of the patient's midpalatal suture. Treatment professionals would benefit from tools that allow them to evaluate and/or visualize how a widening arch would impact a patient's teeth. Treatment professionals would also benefit from tools that allow them to evaluate and/or visualize potential implications of arch and/or palatal expansion to other orthodontic treatments (e.g., malocclusion correction with dental appliances) being implemented in conjunction with arch/palatal expansion. Unfortunately, many tools do not serve these purposes.

SUMMARY OF THE DISCLOSURE

Implementations address the need to provide detailed information about the patient's arch to a dental professional during treatment planning to increase the efficiency and effectiveness of the treatment planning. The present application addresses these and other technical problems by providing technical solutions and/or automated agents that automatically measure and provide the dental arch width to the dental professional during treatment planning. Arch width measurement may provide the basis for implementation of automated orthodontic treatment plans, design and/or manufacture of orthodontic aligners (including series of polymeric orthodontic aligners that provide forces to correct malocclusions in patients' teeth). Dental arch with may also be referred to herein as "inter-arch width."

In general, example apparatuses (e.g., devices, systems, etc.) and/or methods described herein may receive a representation of a patient's teeth, and in some cases clinical information about the patient, to determine the arch width of the patient during treatment and allow the doctor to analyze and modify the treatment plan based on the patient's arch width. The apparatuses and/or methods described herein may provide instructions to generate and/or may generate a set or series of aligners, and/or orthodontic treatment plans using orthodontic aligners that incorporate the changes to arch width made by the dental professional during treatment planning. The apparatuses and/or methods described herein may provide a visual representation of the patient's teeth including arch width.

A "patient," as used herein, may be any subject (e.g., human, non-human, adult, child, etc.) and may be alternatively and equivalently referred to herein as a "patient" or a "subject." A "patient," as used herein, may but need not be a medical patient. A "patient," as used herein, may include a person who receives orthodontic treatment, including orthodontic treatment with a series of orthodontic aligners.

Any of the apparatuses and/or methods described herein may be part of a distal tooth scanning apparatus or method, or may be configured to work with a digital scanning apparatus or method.

As will be described in greater detail herein, automatically determining the width of a patient's arch may include collecting a 3D scan of the patient's teeth. Collecting the 3D scan may include taking the 3D scan, including scanning the patient's dental arch directly (e.g., using an intraoral scanner) or indirectly (e.g., scanning an impression of the patient's teeth), receiving the 3D scan information from a separate device and/or third party, receiving the 3D scan from a memory, or the like.

Additional information may be collected with the 3D scan, including patient information (e.g., age, gender, etc.).

The 3D scan information may be standardized and/or normalized. Standardizing the scan may include converting the 3D scan into a standard format (e.g., a tooth surface mesh), and/or expressing the 3D scan as a number of angles (e.g., vector angles) from a center point of each tooth, etc.

In some variations, standardizing may include normalizing the 3D scan using another tooth, including stored tooth values.

The standardized 3D scan information may then be processed to extract one or more features that may be used to determine the width of the patient's arch; specifically, a tooth crown center on each tooth surface in the coronal direction. This information may be used to automatically and accurately measure and label the arch width of the patient on the 3D model, e.g., by displaying a graphic showing the arch width over images of the 3D model.

Standardizing may include identifying a predetermined number of angles relative to a center point of the target tooth. Any appropriate method may be used to determine the center of the tooth. For example, the center of the tooth may be determined from a mesh point representation of each tooth (e.g., from a segmented version of the 3D scan representing a digital model of the patient's teeth) by determining the geometric center of the mesh points for each tooth, by determining the center of gravity of the segmented tooth, etc. The same method for determining the center of each tooth may be consistently applied between the teeth and any teeth used to form (e.g., train) the systems described herein.

Standardizing may be distinct from normalizing. As used herein, standardizing may involve regularizing numerical and/or other description(s) of a tooth. For example, standardizing may involve regularizing the order and/or number of angles (from the center of the tooth) used to describe the teeth. The sizes of the teeth from the original 3D scan may be maintained.

The 3D scan of the patient's teeth may be collected in any appropriate manner that permits it to be later manipulated by the method or apparatus for standardization, feature extraction and determining the width of the patient's arch. For example, gathering may include taking the 3D model of the patient's teeth directly or indirectly form the patient's teeth. For example, gathering may include receiving a 3D model of the patient's teeth from an intraoral scanner. Gathering may include receiving the 3D model from a scan of a mold of the patient's teeth.

A system (e.g., a system for determining the width of the patient's arch) may include: one or more processors; memory coupled to the one or more processors, the memory configured to store computer-program instructions, that, when executed by the one or more processors, implement a computer-implemented method, the computer-implemented method comprising: gather a three-dimensional (3D) model of a patient's teeth including a target tooth; determine a tooth crown center of each of the patients teeth; determine a width of the patient's arch based on the tooth crown centers; and output the width of the patient's arch. Any of these systems may include a memory for storing the results (e.g., the labeled 3D model of the teeth). Any of these systems may also include an output (e.g., monitor, printer, transmitter, including wireless transmitter), etc.

In any of the apparatuses and/or methods described herein automatically determining a width of the patient's arch may be performed using an apparatus (e.g., computing device) without human control or direction, particularly in the steps of receiving, determining tooth shape features, normalizing, etc. Alternatively or additionally, any of these steps may be performed partially automatically (e.g., semi-autonomously) or manually.

A computing device may receive a three-dimensional (3D) model of the patient's teeth including the target tooth either directly (e.g., as part of a scanning apparatus or system), or indirectly, including transfer from a previously taken model. The computing device may be a dedicated device or part of a dedicated device (e.g., scanner) or it may be wired or wirelessly connected to a scanning device or a memory storing scanning information. Alternatively or additionally, the computing device may receive the 3D model from a remote (e.g., internet, cloud, etc.) source.

In any of the apparatuses and/or methods described herein a target tooth may be user-selected. Alternatively or additionally, all of the teeth in a 3D model of the teeth may be selected as targets; the apparatus and methods may sequentially or concurrently determine width of the patient's arch.

In one aspect, a method of calculating an arch width of a patient is provided, the method comprising receiving, in a computing device, a three-dimensional (3D) model of the patient's teeth including a target tooth, extracting dental features from the 3D model of the patient's arch, determining an arch width between the target tooth and an opposing tooth using the extracted dental features, and outputting from the computing device the arch width.

In one example, outputting the arch width comprises overlaying a graphic with the arch width on the 3D model of the patient's teeth. In one aspect, gathering the 3D model comprises one or more of taking the 3D model of the patient's teeth, receiving the 3D model of the patient's teeth from an intraoral scanner and receiving the 3D model from a scan of a mold of the patient's teeth.

In one example, the target tooth comprises a tooth selected from the group consisting of canine, first bicuspid, first primary molar, second bicuspid, second primary molar, and permanent first molar.

In some examples, determining the arch width is based, at least in part on patient age, eruption status, patient gender, or other patient information associated with the patient.

In another aspect, the method further comprises outputting a modified version of the 3D model of the patient's teeth to include the arch width. The outputted arch width can be utilized as part of an orthodontic treatment plan for the patient's teeth.

In one example, identifying the portion of the 3D model is part of an operation of segmenting the 3D model of the patient's dentition.

In various examples, the extracted dental features can comprise a center of each of the patient's teeth, a lingual edge of each of the patient's teeth, and/or a buccal edge of each of the patient's teeth. In particular, it may be advantageous to measure arch width between a point or region at the intersection of the occlusal surface of a tooth and the long axis of the tooth. The long axis of the tooth may be referred to as the central axis of the tooth.

In one example, after the determining step, the method can further include receiving an input that adjusts a position or rotation of the target tooth, and repeating determining the arch width between the target tooth and the opposing tooth using the extracted dental features.

For example, described herein are computer-implemented methods (and systems for performing these methods) comprising: displaying a three-dimensional (3D) model of a patient's dentition for one or more of: a patient's initial tooth position and a patient's modified tooth position; determining, for each of the patient's initial tooth position and the patient's modified tooth position, an arch width measurement between one or more pairs of teeth in the patient's dental arch, wherein the arch width measurement for each pair of teeth of the one or more pairs of teeth is determined between a first point at an intersection of a first occlusal surface and a long axis of a first tooth of the pair of teeth and a second point at an intersection of a second occlusal surface and a long axis of a second tooth of the pair of teeth; and displaying (e.g., as a table) the arch width measurements. Any of these methods and systems may include updating the arch width measurements displayed in the table as a user changes the patient's modified tooth position. Updating the arch width measurements displayed in the table may comprise updating the arch width measurements in real time as the user changes the patient's modified tooth position.

Updating the arch width measurements displayed in the table may comprise updating the arch width measurements as the user changes a position of one or more teeth in 3D model of the patient's modified tooth position. In some variations a user may use a tool (e.g., a graphical user interface tool) to manipulate the position and/or orientation of a tooth or teeth on the 3D model displayed. The arch width measurements may be updated to reflect the changes in the arch width made by manipulating the teeth. Alternatively or additionally, the user may toggle or switch between displays of different stages of a treatment plan (in which the positions of the teeth have changed relative to the patient's initial tooth positions), and the dental arch width measurements may be updated to reflect the change. For example, the 3D model of the patient's modified tooth position may include a 3D model of the patient's dentition for one stage of a multi-stage orthodontic treatment plan.

Determining the arch width measurement between one or more pairs of teeth in the patient's dental arch may comprise determining arch width measurements for all or some of: an arch width between the patient's canines, an arch width between the patient's first premolars or between the patient's first primary molars, an arch width between the patient's second premolars or between the patient's second primary molars, and an arch width between the patient's permanent first molars.

Any of these methods may also include determining, for a calculated modified tooth position, an arch width measurement between one or more pairs of teeth in the patient's dental arch of the calculated modified tooth position. The arch width measurements for the patient's initial tooth position, the patient's modified tooth position, and the calculated modified tooth position (e.g., a proposed or ideal modified tooth position) may be displayed (e.g., in a table) the arch widths.

The arch width measurements may be displayed as a table or chart and/or may be displayed directly onto the model(s) of the dentition. For example, displaying a table of the arch width measurements may include displaying the table on or adjacent to the 3D model of the patient's dentition. Displaying may include displaying differences between the arch widths for the patient's initial tooth position and the patient's modified tooth position (e.g., shown as a difference (+/−) in these measurements).

Displaying a three-dimensional (3D) model of a patient's dentition may include displaying a user-manipulatable image of a 3D model of the patient's modified tooth position. User-manipulatable may include changing the view (display), e.g., by rotating, zooming in/out, tilting, separating the upper/lower aches, and/or ins some variations, changing the position and/or orientation of one or more of the teeth in the dental arch.

Updating the arch width measurements displayed in the table as the user changes the patient's modified tooth position may comprise updating the arch width measurements displayed for the patient's modified tooth position as the user selects different stages of a multi-stage orthodontic treatment plan.

Also described herein are methods and apparatuses (e.g., systems) for estimating, displaying, and/or modifying arch width between one or more pairs of a patient's teeth. For example, a method may include providing a treatment plan with a first plurality of treatment stages to move a patient's teeth from an initial arrangement (e.g., toward a target arrangement) through a plurality of intermediate arrangements, the first plurality of treatment stages comprising a second plurality of treatment stages, and the patient's teeth having at least one arch; providing a virtual model of the patient's teeth, the virtual model representing the patient's teeth in accordance with the first plurality of treatment stages; locating on the virtual model a plurality of anatomical reference points on the patient's teeth for an arch width measurement; for each of the second plurality of treatment stages: calculating an estimated arch width of the at least one arch using distances between the plurality of anatomical reference points, the estimated arch width being specific to the each of the second plurality of treatment stages; and outputting a virtual representation of the estimated arch width.

A method may include: locating a plurality of anatomical reference points on a patient's teeth for an arch width measurement on a virtual model of a patients teeth (e.g., a virtual model representing the patient's teeth in accordance with a first plurality of treatment stages of a treatment plan, such as a treatment plan to move a patient's teeth from an initial arrangement toward a target arrangement through a plurality of intermediate arrangements), and for each of a second plurality of treatment stages: calculating an estimated arch width of the at least one arch using distances between the plurality of anatomical reference points, the estimated arch width being specific to the each of the second plurality of treatment stages; and outputting a virtual representation of the estimated arch width.

Locating the one or more anatomical reference points on the virtual model may include: determining from the virtual model whether one or more anatomical reference points of the plurality of anatomical reference points correspond to a mix of permanent and primary teeth; if the one or more anatomical reference points correspond to a mix of the permanent and the primary teeth, using locations of the permanent teeth as the basis of one or more of the anatomical reference points.

Any of these methods may also include determining from the virtual model whether one or more anatomical reference points of the plurality of anatomical reference points correspond to abnormal dental structures; calculating the estimated arch width comprises ignoring the abnormal teeth if the one or more anatomical reference points of the plurality of anatomical reference points correspond to abnormal teeth.

The method may also include determining from the virtual model whether one or more anatomical reference points of the plurality of anatomical reference points correspond to abnormal teeth; calculating the estimated arch width comprises ignoring the abnormal teeth if the one or more anatomical reference points of the plurality of anatomical reference points correspond to abnormal teeth; the abnormal dental structures correspond to one or more of supernumerary teeth, pontics, tooth gaps after an extraction operation, and a partially erupted tooth.

The plurality of anatomical reference points may include projections of tooth crown centers in a coronal direction.

The plurality of anatomical reference points may include points on opposing canines, opposing first bicuspids, opposing first molars, opposing second bicuspids, opposing second primary molars, opposing permanent first molars, or some combination thereof.

The plurality of anatomical reference points may be anatomical reference point pairs taken from opposing teeth of an arch of the patient's teeth. The estimated arch width may include determining a minimum distance between one or more of the plurality of anatomical reference points.

Calculating the estimated arch width may include determining a minimum distance between one or more of the plurality of anatomical reference points; and the plurality of anatomical reference points are anatomical reference point pairs taken from opposing teeth of an arch of the patient's teeth. Calculating the estimated arch width may include determining distances between the plurality of anatomical reference points based on the initial arrangement of the patient's teeth. Calculating the estimated arch width may comprise determining distances between the plurality of anatomical reference points based on the initial arrangement of the patient's teeth; and the initial arrangement corresponds to a scan of the patient's teeth.

Any of these methods may include performing a scan of the patient's teeth before providing the treatment plan. The method may include displaying the virtual representation of the estimated arch width for each of the second plurality of treatment stages. Any of these methods may include displaying, alongside a representation of the virtual model, the virtual representation of the estimated arch width for each of the second plurality of treatment stages. The methods may include displaying the plurality of anatomical reference points for each of the second plurality of treatment stages.

For example, a method may include providing a treatment plan with a first plurality of treatment stages to move a patient's teeth from an initial arrangement toward a target arrangement through a plurality of intermediate arrangements, the first plurality of treatment stages comprising a second plurality of treatment stages, and the patient's teeth having at least one arch; providing a virtual model of the patient's teeth, the virtual model representing the patient's teeth in accordance with the first plurality of treatment stages; locating on the virtual model a plurality of anatomical reference points on the patient's teeth for an arch width measurement; for each of the second plurality of treatment stages: calculating an estimated arch width of the at least one arch using distances between the plurality of anatomical reference points, the estimated arch width being specific to the each of the second plurality of treatment stages; outputting a virtual representation of the estimated arch width, wherein: the second plurality of treatment stages comprises a first treatment stage corresponding to a first arrangement of the patient's teeth and a second treatment stage corresponding to a second arrangement of the patient's teeth; the method further comprises: receiving a modification request to modify the first arrangement; updating the virtual model of the patient's teeth based on the modification request; for each of the second plurality of treatment stages: recalculating the estimated arch width using updated distances between the plurality of anatomical reference points; and outputting a virtual representation of a recalculated estimated arch width.

As mentioned, the first arrangement may comprise the target arrangement and the second arrangement may comprise a specific intermediate arrangement of one of the plurality of intermediate arrangements. Any of these methods may include displaying the virtual representation of the estimated arch width for each of the plurality of treatment stages for each of the second plurality of treatment stages, and/or displaying the plurality of anatomical reference points for each of the second plurality of treatment stages.

A system may include: one or more processors; memory coupled to the one or more processors, the memory configured to store computer-program instructions, that, when executed by the one or more processors, implement a computer-implemented method, the computer-implemented method comprising: providing a virtual model of the patient's teeth, the virtual model representing the patient's teeth in accordance with the first plurality of treatment stages; locating on the virtual model a plurality of anatomical reference points on the patient's teeth for an arch width measurement; for each of the second plurality of treatment stages: calculating an estimated arch width of the at least one arch using distances between the plurality of anatomical reference points, the estimated arch width being specific to the each of the second plurality of treatment stages; and outputting a virtual representation of the estimated arch width.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
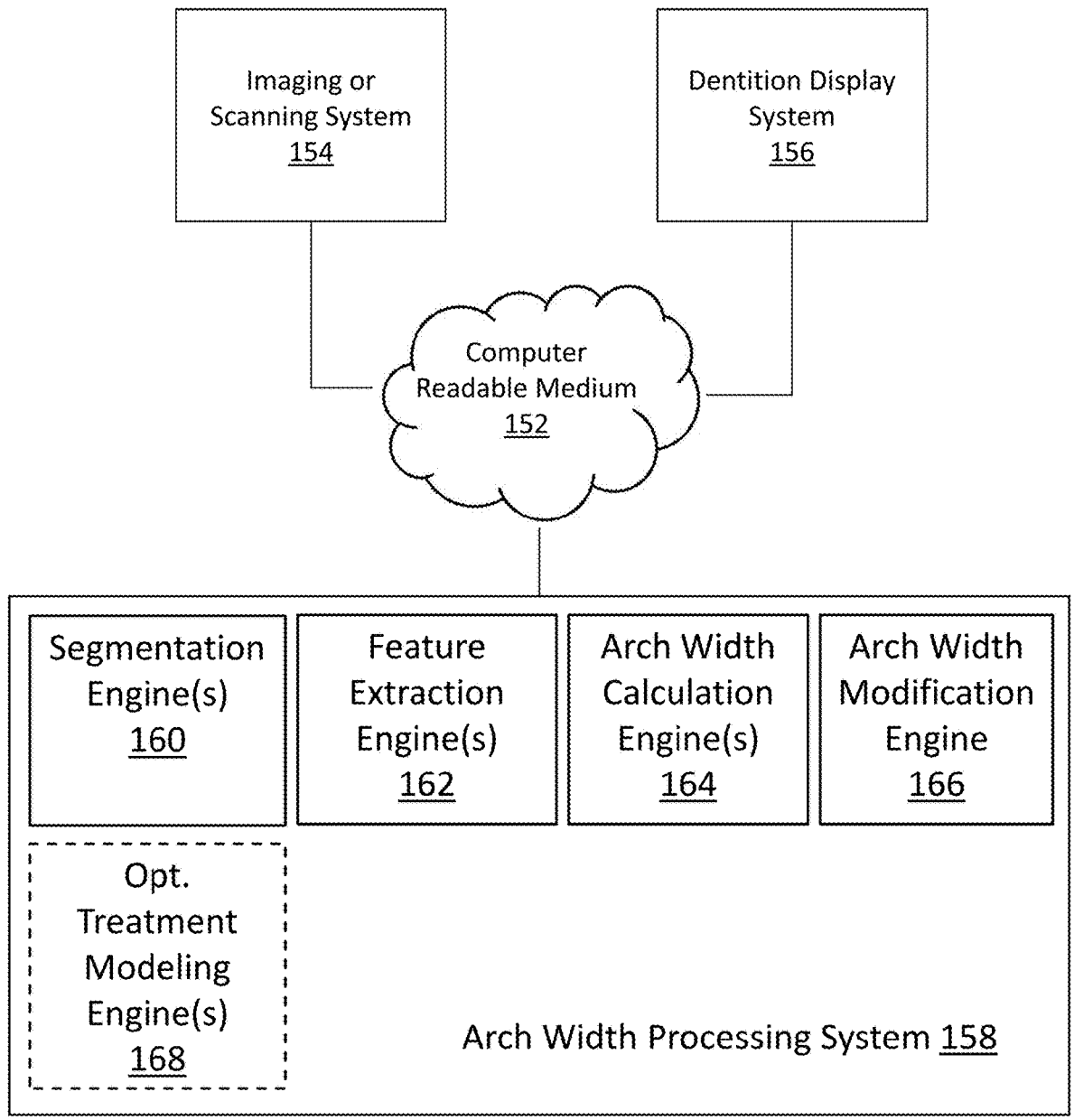
FIG. 1A is a diagram showing an example of a computing environment configured to digitally scan a dental arch and determine a width of a patient's arch.

The methods and apparatuses described herein may improve treatment planning, including potentially increasing the speed at which treatment plans may be completed, as well as providing greater choices, information about the dental arch, and control to the dental professional, and allowing improved patient involvement in the treatment planning process.

Described herein are apparatuses (e.g., systems, computing device readable media, devices, etc.) and methods for determining a width of a patient's arch, and using the arch width for dental treatment planning. These methods and apparatus can use this information to provide output to a patient, physician, dental technician, or the like. These apparatuses and/or methods may be further configured to use the arch width in forming one or more orthodontic devices (e.g., one or more, including a set, of aligners), treatment plans, or some combination of these.

The apparatuses and/or methods described herein may be useful in planning and fabrication of dental appliances, including elastic polymeric positioning appliances, is described in detail in U.S. Pat. No. 5,975,893, and in published PCT Application WO 98/58596, which is herein incorporated by reference for all purposes. Systems of dental appliances employing technology described in U.S. Pat. No. 5,975,893 are commercially available from Align Technology, Inc., Santa Clara, Calif., under the tradename, Invisalign System.

Throughout the body of the Description of Embodiments, the use of the terms "orthodontic aligner", "aligner", or "dental aligner" is synonymous with the use of the terms "appliance" and "dental appliance" in terms of dental applications. For purposes of clarity, embodiments are hereinafter described within the context of the use and application of appliances, and more specifically "dental appliances."

The apparatuses and/or methods (e.g., systems, devices, etc.) described below can be used with and/or integrated into an orthodontic treatment plan. The apparatuses and/or methods described herein may be used to segment a patient's teeth from a two-dimensional image and this segmentation information may be used to simulate, modify and/or choose between various orthodontic treatment plans. Segmenting the patient's teeth can be done automatically (e.g., using a computing device). For example, segmentation can be performed by a computing system automatically by evaluating data (such as three-dimensional scan, or a dental impression) of the patient's teeth or arch.

As described herein, an intraoral scanner may image a patient's dental arch and generate a virtual three-dimensional model of that dental arch. During an intraoral scan procedure (also referred to as a scan session), a user (e.g., a dental practitioner) of an intraoral scanner may generate multiple different images (also referred to as scans or medical images) of a dental site, model of a dental site, or other object. The images may be discrete images (e.g., point-and-shoot images) or frames from a video (e.g., a continuous scan). The three-dimensional scan can generate a 3D mesh of points representing the patient's arch, including the patient's teeth and gums. Further computer processing can segment or separate the 3D mesh of points into individual teeth and gums.

An automated arch width processing system, as used herein, may include a system that uses automated agents to identify and/or number individual teeth and/or dental features of virtual representations of teeth, such as teeth represented in a three-dimensional dental mesh model resulting from a digital scan.

The present disclosure presents one or more novel processes for identifying and segmenting a patient's teeth during an identification process. Some implementations herein may solve technical problems related to optimizing and/or increasing the accuracy of digital dental scanning technologies.

FIG. 1A is a diagram showing an example of a computing environment 100A configured to facilitate gathering digital scans of a dental arch with teeth therein. The environment 100A includes a computer-readable medium 152, a scanning system 154, a dentition display system 156, and an arch width processing system 158. One or more of the modules in the computing environment 100A may be coupled to one another or to modules not explicitly shown.

The computer-readable medium 152 and other computer readable media discussed herein are intended to represent a variety of potentially applicable technologies. For example, the computer-readable medium 152 can be used to form a network or part of a network. Where two components are co-located on a device, the computer-readable medium 152 can include a bus or other data conduit or plane. Where a first component is co-located on one device and a second component is located on a different device, the computer-readable medium 152 can include a wireless or wired back-end network or LAN. The computer-readable medium 152 can also encompass a relevant portion of a WAN or other network, if applicable.

The scanning system 154 may include a computer system configured to scan a patient's dental arch. A "dental arch," as used herein, may include at least a portion of a patient's dentition formed by the patient's maxillary and/or mandibular teeth, when viewed from an occlusal perspective. A dental arch may include one or more maxillary or mandibular teeth of a patient, such as all teeth on the maxilla or mandible or a patient. The scanning system 154 may include memory, one or more processors, and/or sensors to detect contours on a patient's dental arch. The scanning system 154 may be implemented as a camera, an intraoral scanner, an x-ray device, an infrared device, etc. The scanning system 154 may include a system configured to provide a virtual representation of a physical mold of patient's dental arch. The scanning system 154 may be used as part of an orthodontic treatment plan. In some implementations, the scanning system 154 is configured to capture a patient's dental arch at a beginning stage, an intermediate stage, etc. of an orthodontic treatment plan.

The dentition display system 156 may include a computer system configured to display at least a portion of a dentition of a patient. The dentition display system 154 may include memory, one or more processors, and a display device to display the patient's dentition. The dentition display system 156 may be implemented as part of a computer system, a display of a dedicated intraoral scanner, etc. In some implementations, the dentition display system 156 facilitates display of a patient's dentition using scans that are taken at an earlier date and/or at a remote location. It is noted the dentition display system 156 may facilitate display of scans taken contemporaneously and/or locally to it as well. As noted herein, the dentition display system 156 may be configured to display the intended or actual results of an orthodontic treatment plan applied to a dental arch scanned by the scanning system 154. The results may include 3D virtual representations of the dental arch, 2D images or renditions of the dental arch, etc. The dentition display system 156 may further include an input device that allows a dental professional to interact with the 3D or 2D virtual representations of the dental arch. In some examples, the display itself can comprise an input device (e.g., a touch screen display). In other examples, a separate input device such as a controller, keyboard, mouse, joystick, or the like may be used to interact with the contents of the display.

The arch width processing system 158 may include a computer system configured to process 3D scans or meshes of a patient's dentition taken by the scanning system 154. As noted herein, the arch width processing system 158 may be configured to process scans of teeth in a dental arch. The arch width processing system 158 may include segmentation engine(s) 160, feature extraction engine(s) 162, arch width calculation engine(s) 164, arch modification engine(s) 166, and optional treatment modeling engine(s) 168. One or more of the modules of the arch width processing system 158 may be coupled to each other or to modules not shown.

As used herein, any "engine" may include one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, "datastores" may include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

The segmentation engine(s) 160 may be configured to implement one or more automated agents configured to process tooth scans from the scanning system 154. The segmentation engine(s) 160 may include graphics engines to process images or scans of a dental arch. In some implementations, the segmentation engine(s) 160 format scan data from an scan of a dental arch into a dental mesh model (e.g., a 3D dental mesh model) of the dental arch. The segmentation engine(s) 160 may also be configured to segment the 3D dental mesh model of the dental arch into individual dental components, including segmenting the 3D dental mesh model into 3D mesh models of individual teeth. The 3D dental mesh models of the dental arch and/or the individual teeth may comprise geometric point clouds or polyhedral objects that depict teeth and/or other elements of the dental arch in a format that can be rendered on the dentition display system 156. The segmentation engine(s) 160 may provide 3D dental mesh models and/or other data to other modules of the arch width processing system 158.

The feature extraction engine(s) 162 may implement one or more automated agents configured to extract dental features. A "dental feature," as used herein, may include data points from the 3D dental mesh model that correlate to edges, contours, vertices, vectors, centers, or surfaces of the patient's teeth. A "dental feature" may be based on patient demographics and/or tooth measurements. The feature extraction engine(s) 162 may also implement one or more automated agents configured to determine and identify the center of each tooth in the dental arch. The feature extraction engine 162 may, for example, apply various techniques such as geometric center, weighted center, etc., to find the center of the individual tooth segmentation data.

The arch width calculation engine(s) 164 may implement one or more automated agents configured to calculate one or more widths of a patient's arch. In some implementations, the arch width calculation engine(s) 164 assign physical and/or geometrical properties to a 3D dental mesh model that are related to physical/geometrical properties of dental arches or teeth. The arch width calculation engine(s) 164 may receive dental features from feature extraction engine(s) 162 and apply algorithms to determine the width(s) of the patient's arch. The arch width calculation engine(s) 164 can incorporate the arch width into all stages of the treatment planning, including the initial segmentation, intermediate segmentations, and a final segmentation result.

The arch width calculation engine(s) 164 may also output a final segmentation result to other modules, for example, the arch modification engine(s) 166 or the optional treatment modeling engine(s) 168.

The arch modification engine(s) 166 may implement one or more automated agents configured to present the arch width to a dental professional at each stage of the treatment planning and allow the dental professional to modify the teeth position and/or arch width. The arch modification engine(s) will automatically re-calculate arch width values for the remaining treatment when the tooth position or arch width is modified. In some implementations, the dental professional can interact with the dentition display system 156 (e.g., by manipulating an input device) to modify the teeth position and/or arch width. The modifications can be calculated and displayed in real-time for the dental professional to see the effect of the modifications.

The optional treatment modeling engine(s) 168 may be configured to store and/or provide instructions to implement orthodontic treatment plans and/or the results of orthodontic treatment plans. The optional treatment modeling engine(s) 168 may provide the results of orthodontic treatment plans on a 3D dental mesh model. The optional treatment modeling engine(s) 166 may model the results of application of orthodontic aligners to the patient's dental arch over the course of an orthodontic treatment plan.

Figure 1B:
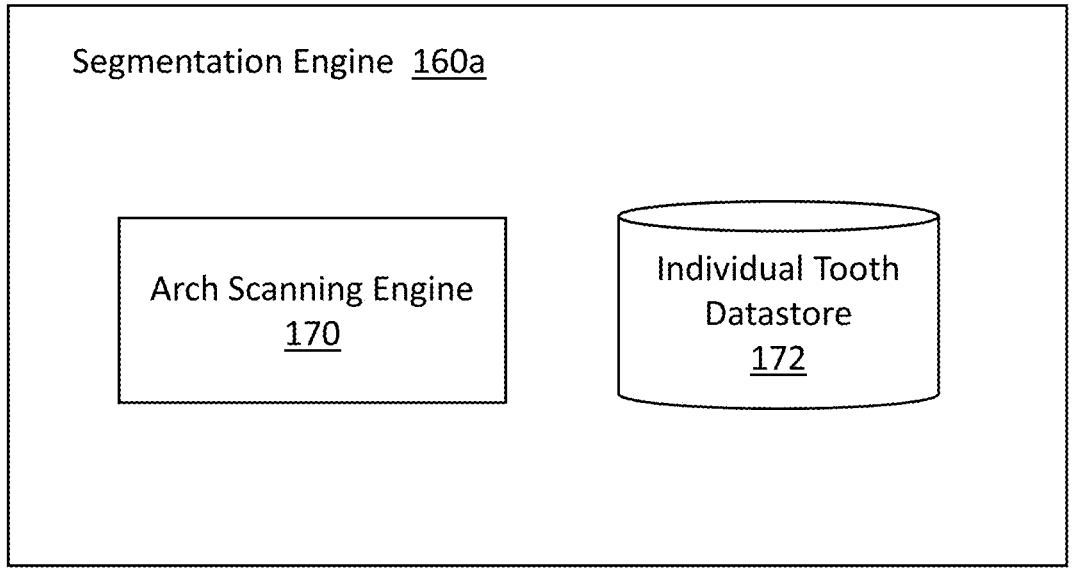
FIG. 1B is a diagram showing an example of segmentation engine(s).

FIG. 1B is a diagram showing an example of the segmentation engine(s) 160a. The segmentation engine(s) 160a may include an arch scanning engine 170 and an individual tooth segmentation datastore 172. One or more of the modules of the segmentation engine(s) 160a may be coupled to each other or to modules not shown.

The arch scanning engine 170 may implement one or more automated agents configured to scan a 3D dental mesh model for individual tooth segmentation data. "Individual tooth segmentation data," as used herein, may include positions, geometrical properties (contours, etc.), and/or other data that can form the basis of segmenting individual teeth from 3D dental mesh models of a patient's dental arch. The arch scanning engine 170 may implement automated agents to separate dental mesh data for individual teeth from a 3D dental mesh model of the dental arch. The arch scanning engine 170 may further implement automated agents to number the individual teeth.

The individual tooth segmentation datastore 172 may be configured to store data related to model dental arches, including model dental arches that have been segmented into individual teeth. The model dental arch data may comprise data related to segmented individual teeth, including tooth identifiers of the individual teeth such as tooth types, tooth numbers, and eruption status(es).

Figure 1C:
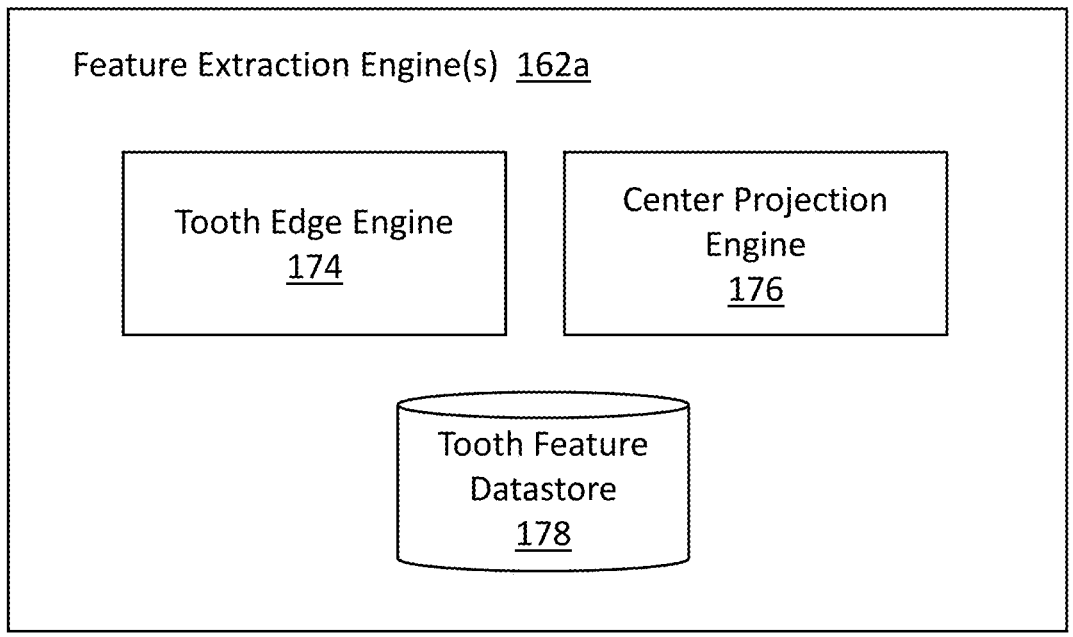
FIG. 1C is a diagram showing an example of a feature extraction engine(s).

FIG. 1C is a diagram showing an example of the feature extraction engine(s) 162a. The feature extraction engine(s) 162a may include tooth edge engine 174, a center projection engine 176, and a tooth feature datastore 178. One or more of the modules of the feature extraction engine(s) 162a may be coupled to each other or to modules not shown.

The tooth edge engine 174 may implement one or more automated agents configured to find edges or other noteworthy features of the individual tooth segmentation data. The tooth edge engine 174 may, for example, apply various techniques such as edge detection algorithms to find the edges, tooth lines, and gingiva lines of the individual tooth segmentation data. The tooth edge engine 174 can store the data in the tooth feature datastore 176.

Figure 6:
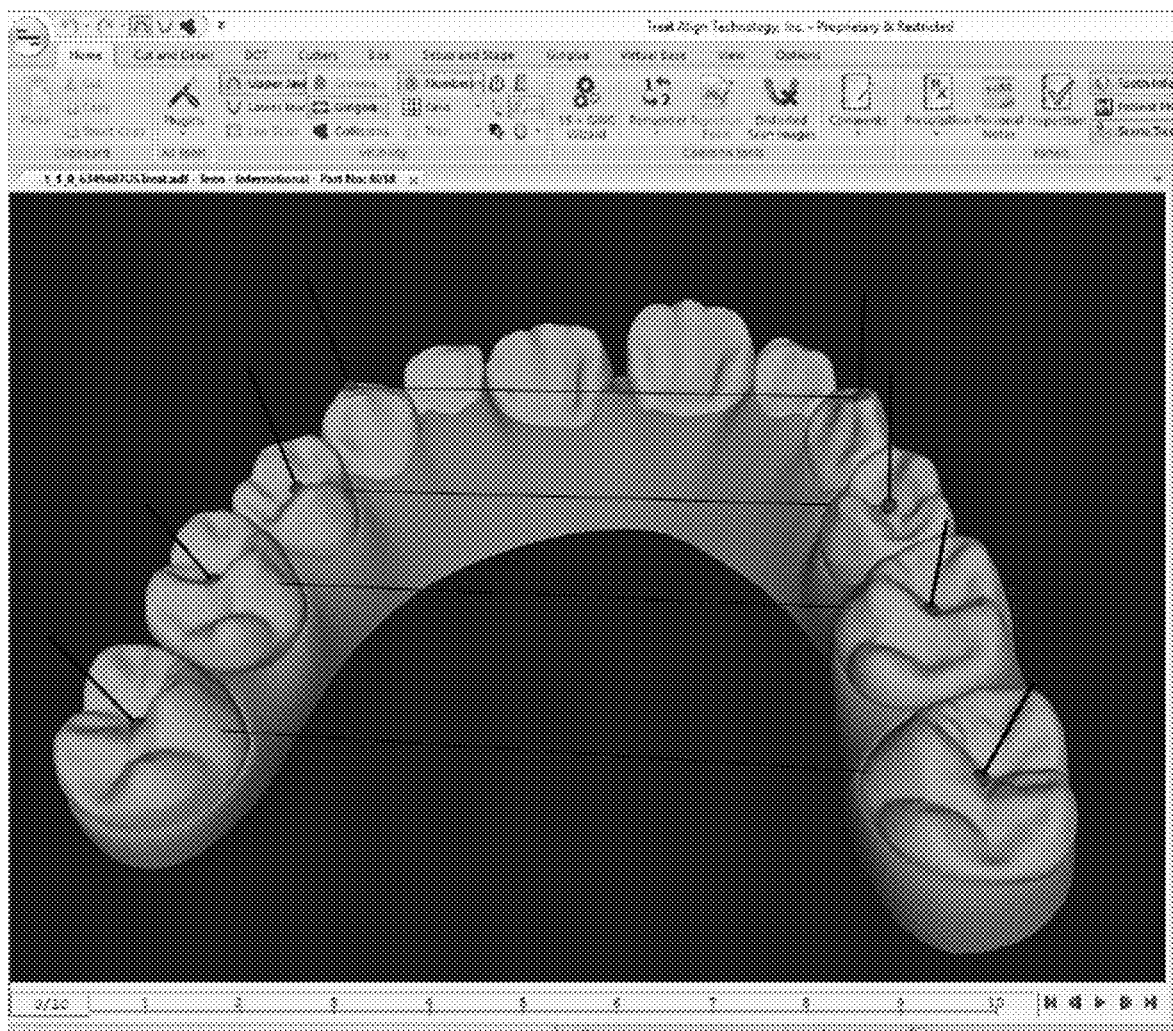
FIG. 6 is an example of a 3D model of a dental arch with the arch widths displayed between the centers of opposing teeth.

The center projection engine 176 may implement one or more automated agents configured to find the appropriate center of the individual tooth segmentation data. The center projection engine 174 may, for example, apply various techniques such as geometric center, weighted center, etc., to find the center of the individual tooth segmentation data. FIG. 6 shows an example of a 3D dental model with the geometric centers of individual teeth identified. The center projection engine 174 can store the center data in the tooth feature datastore 176.

The tooth feature datastore 176 may be configured to store data related to teeth features, including vectors representing the tooth shape and edge or center data representing the edges or center of the individual tooth segmentation data. In some implementations, only a subset of the total tooth features, such as the vectors representing tooth shape, are stored in the tooth feature datastore.

Figure 1D:
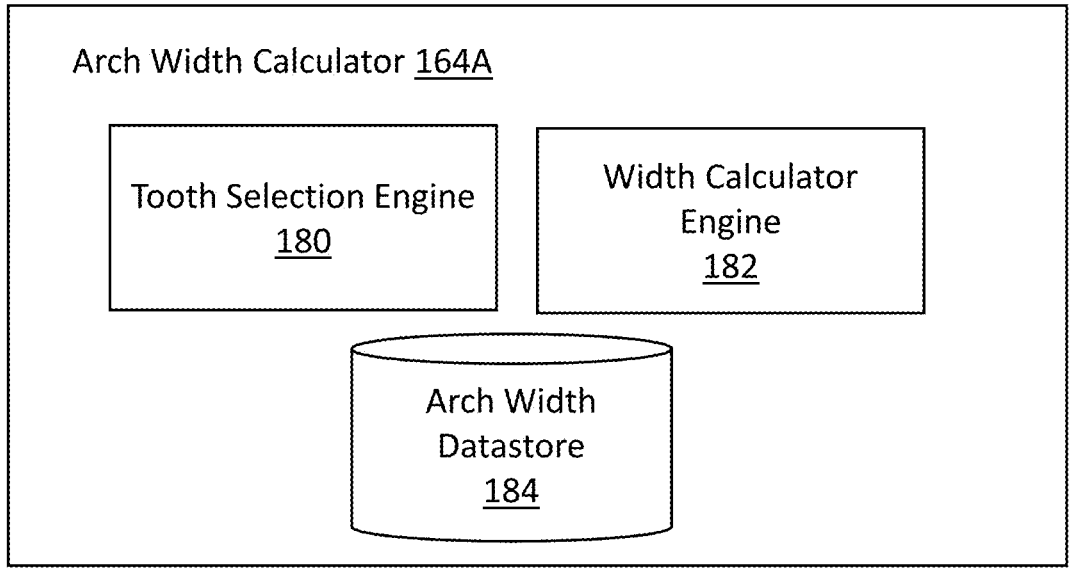
FIG. 1D is a diagram showing an example of an arch width calculation engine(s).

FIG. 1D is a diagram showing an example of the arch width calculation engine(s) 164a. The arch width calculation engine(s) 164a may receive teeth features, teeth centers, and/or tooth shape features from the feature extraction engine(s) 162a described above, and determine the width of the patient's arch in one or more positions. The arch width calculation engine(s) 164a may include tooth selection engine 180, a width calculation engine 182, and an arch width datastore 184.

The tooth selection engine 180 may be configured to identify the proper pairs of teeth in the patient's arch for arch measurement. In some implementations, the tooth selection engine 180 selects individual tooth segmentation data relating to the pairs of teeth for which the arch width is to be measured and displayed. In one implementation, the tooth selection engine 180 identifies a target tooth and the tooth opposing the target tooth, including opposing canines, first bicuspids or first primary molars, second bicuspids or second primary molars, and permanent first molars. In one implementation, if both permanent and primary teeth are present in the patient's arch, then the tooth selection engine 180 can use only the permanent teeth for arch width calculation. Some teeth can be ignored in the arch width calculation, including supernumerary teeth, pontic teeth, teeth after extraction, and partially erupted teeth.

The width calculation engine 182 may be configured to calculate the width of the patient's arch by determining the distance between the opposing teeth identified by the tooth selection engine 180. The width calculation engine 182 can use the feature data from the feature extraction engine to determine a distance between the selected opposing teeth (e.g., between opposing canines or opposing permanent first molars). In some implementations, the distance is calculated between the tooth crown on the tooth surface in the coronal direction between the opposing teeth of the same type (e.g., the distance between the crown center of a permanent first molar and the crown center of its opposing permanent first molar). In some implementations, other features of the teeth can be used to determine the distance. For example, the buccal edges of the target teeth can be used to determine the distance, or alternatively, the lingual edges of the target teeth can be used. Any identified features of the teeth can be used to determine the arch width so long as the chosen features are applied consistently between the target tooth and its opposing tooth. However, using the center of the teeth as the feature has the advantage of providing an accurate measurement of arch width without being affected by tooth rotation.

The arch width datastore 184 may be configured to store data related to the arch width, including the calculated widths between all qualified opposing teeth. For example, the arch width datastore may be configured to store data relating to a width between opposing canines, opposing first bicuspids or first primary molars, opposing second bicuspids or second primary molars, and opposing permanent first molars.

Figure 1E:
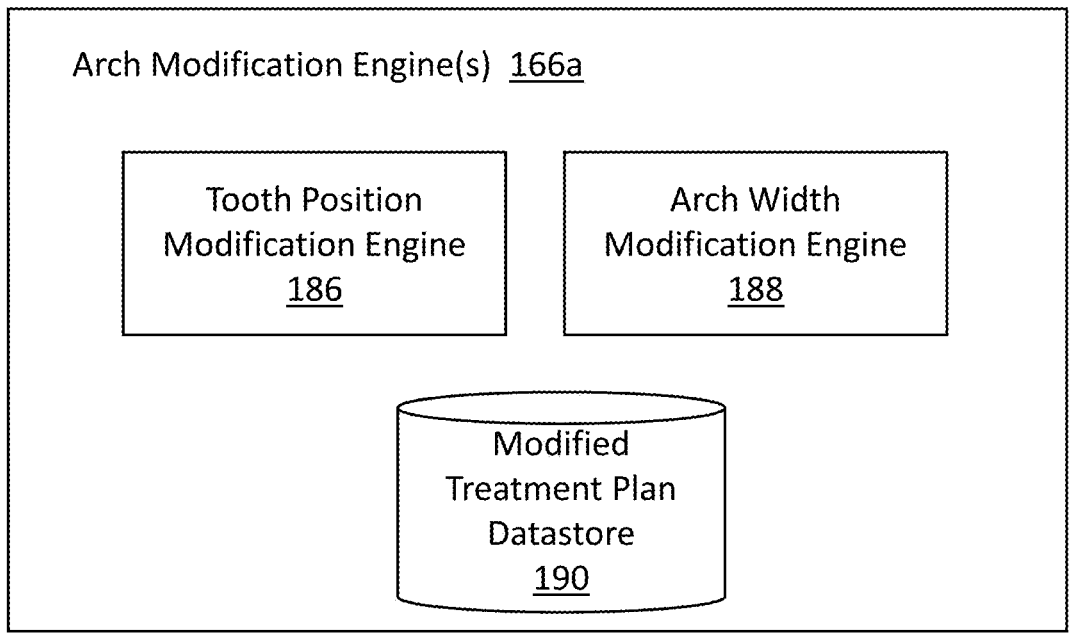
FIG. 1E is a diagram showing an example of an arch modification engine(s).

FIG. 1E is a diagram showing an example of the arch modification engine(s) 166a. The arch modification engine(s) 166a may automatically update a treatment plan and display it in real time (via the dentition display system) in response to modifications from a dental professional. The arch modification engine(s) 166a may include a tooth position modification engine 186, an arch width modification engine 188, and a modified treatment plan datastore 190.

The tooth position modification engine 186 may be configured to receive input or modification from a dental professional changing or adjusting the position or orientation of individual teeth. The individual tooth position and/or orientation can be modified or changed by the dental professional at any stage of the treatment, including the final position. The tooth position modification engine 186 can communicate with the optional treatment modeling engine 168 to incorporate the modifications into the overall treatment plan for the patient.

The arch width modification engine 188 may be configured to receive input or modification from a dental professional changing or adjusting the width of the patient's arch. The width between opposing teeth, such as opposing canines, opposing first bicuspids or first primary molars, opposing second bicuspids or second primary molars, and opposing permanent first molars can be modified or changed by the dental professional at any stage of the treatment, including the final position. In some examples, the dental professional can move, rotate, or adjust the position of an individual tooth, and the arch width modification engine can be configured to re-calculate the arch width of the patient based on the adjustment. The arch width modification engine 188 can communicate with the optional treatment modeling engine 168 to incorporate the modifications into the overall treatment plan for the patient.

The modified treatment plan datastore 190 may be configured to store data related to the modifications made by the dental professional, including modifications to tooth position, tooth orientation, or arch width. For example, the arch width datastore may be configured to store data relating to changes or modifications to the width between opposing canines, opposing first bicuspids or first primary molars, opposing second bicuspids or second primary molars, and opposing permanent first molars.

Figure 2:
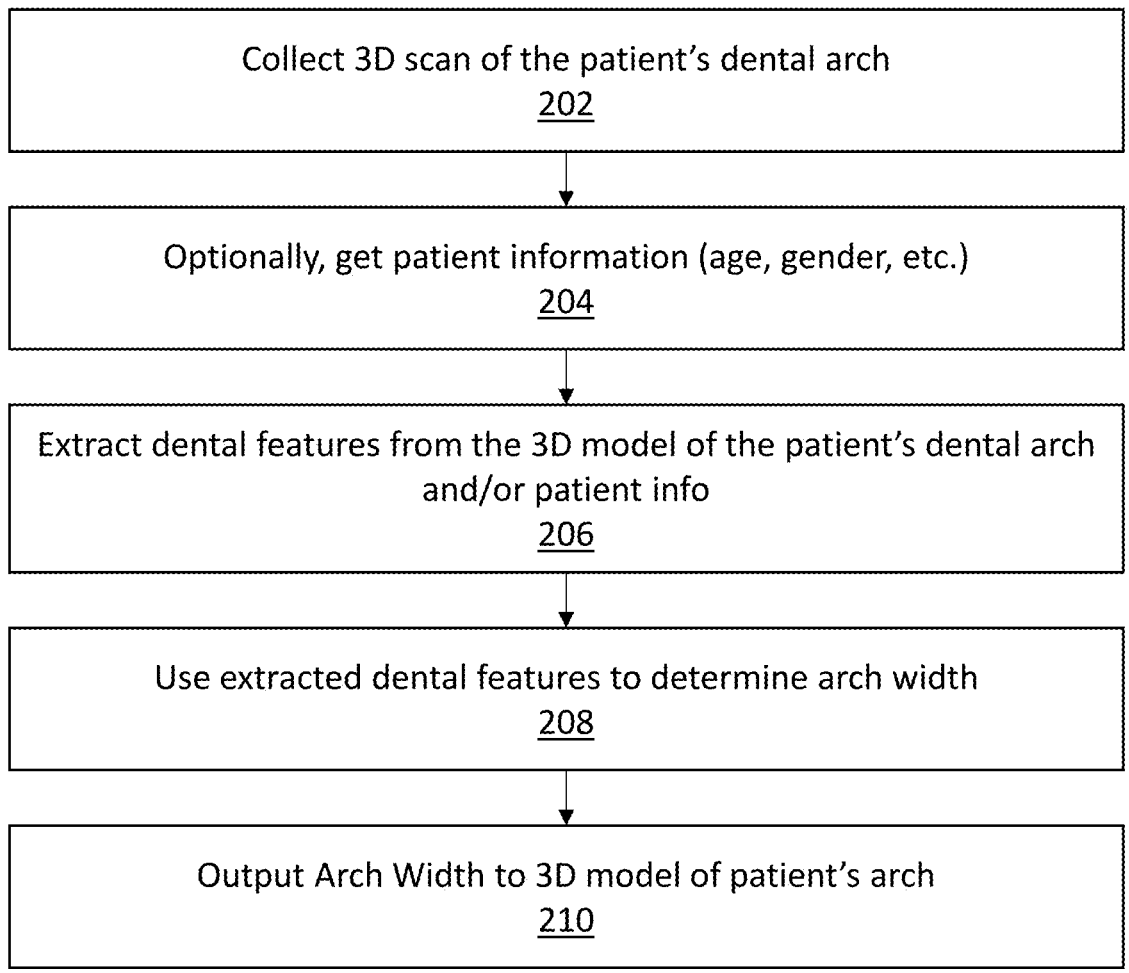
FIG. 2 is an example of a method of automatically determining the width of a patient's arch.

FIG. 2 illustrates one example of a method 200 for automatically determining the width of a patient's dental arch. This method may be automatically implemented by a system, such as one or more of the systems in the computing environment 100A, shown in FIG. 1A. At an operation 202, the system may automatically collect a three-dimensional (3D) scan of the patient's dental arch. The 3D scan may be collected directly from the patient (e.g., using an intraoral scanner) or indirectly (e.g., by scanning a mold of the patient's dentition and/or be receiving a digital model of the patient taken by another, etc.). Optionally, at an operation 204, additional information about the patient may be collected (directly or indirectly), such as the patient's age, gender, etc. For example, the patient's age may be useful in determining which teeth to use to calculate arch width (e.g., first bicuspids or first primary molars).

In some implementations, the 3D scan may be prepared for further processing. For example, the 3D scan may be expressed as a digital mesh and/or segmented into individual teeth (and non-teeth elements, such as gingiva, arch, etc.).

At an operation 206, dental features may be extracted from the 3D model of the patient's teeth (and in some variations from additional data about the patient or the patient's teeth), e.g., using a feature extraction engine. For example, in some variations extraction of features may include determining a center of each of the patient's teeth, or automatically detecting the edges of the patient's teeth such as the buccal or lingual edges of the patient's teeth.

At an operation 208, extracted dental features (e.g., crown center of each tooth) may be used exclusively or in combination with any other extracted feature described herein. The extracted dental features may be provided to the width calculation engine to determine the arch width of the patient's arch at between at least one set of opposing teeth (e.g., between opposing canines, opposing first bicuspids or first primary molars, opposing second bicuspids or second primary molars, and opposing permanent first molars).

At an operation 210, the width of the patient's dental arch may then be output. In some variations this information is used to modify a model (e.g., a 3D digital model) of the patient's teeth (e.g., dental arch). For example, each tooth may be labeled and/or referenced by a name or number (or other alphanumeric) that corresponds to the arch width. For example, the tooth may be automatically and accurately labeled using these methods and systems in a numbering standard (e.g., a universal number system or a modified universal numbering system) that further indicates arch width. Alternative standard dental numbering systems may be used (e.g., FDI World Dental Federation notation, Palmer notation, etc.).

Figure 3:
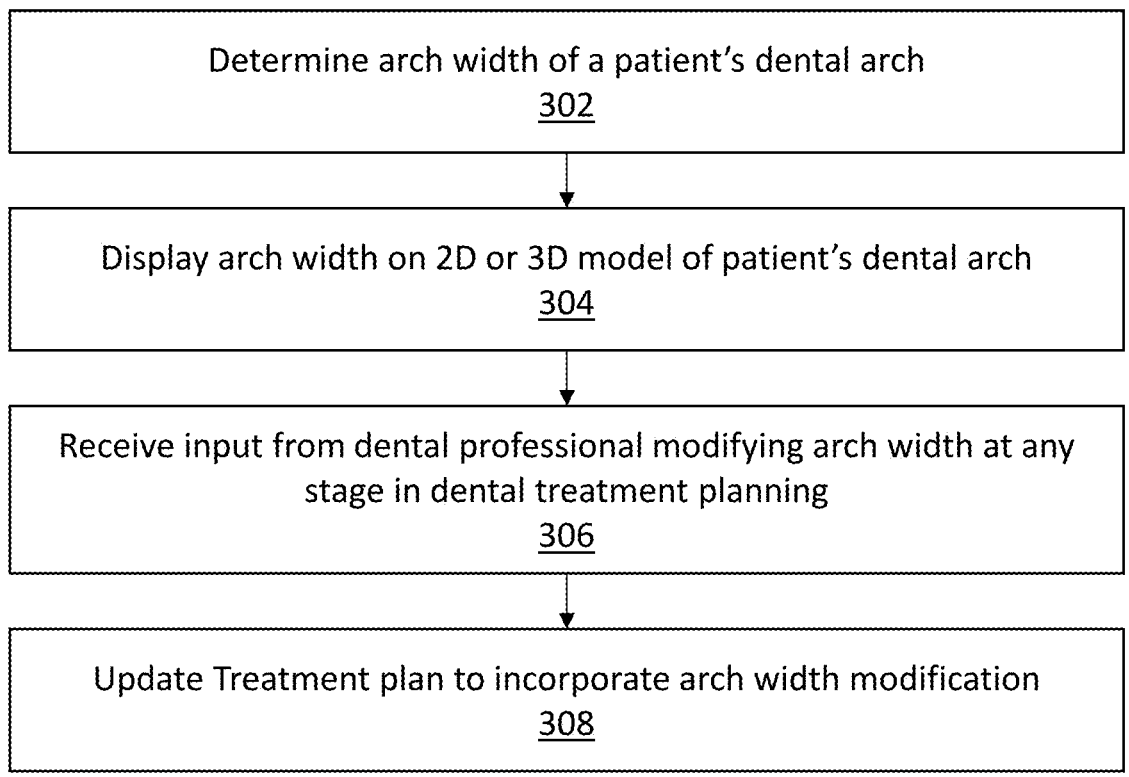
FIG. 3 is an example of a method of using an arch width for dental treatment planning.

FIG. 3 illustrates one example of a method 300 for modifying an arch width of a patient's dental arch and incorporating the modified arch width into dental treatment planning. This method may be automatically implemented by a system, such as one or more of the systems in the computing environment 100A, shown in FIG. 1A. At an operation 302, the system may determine an arch width of a patient's dental arch. This can be, for example the arch width determined and described above in FIG. 2.

At an operation 304, the arch width can be displayed on a 2D or 3D model of the patient's dental arch. In some implementations, multiple arch widths can be displayed on the dental model. For example, the distance between opposing canines, opposing first bicuspids or first primary molars, opposing second bicuspids or second primary molars, and opposing permanent first molars can be displayed on the dental model.

At an operation 306, the system can receive input from a dental professional modifying the arch width at any stage in the dental treatment planning. For example, a dental professional can input (e.g., via an input device such as a touch screen display), changes to the dental arch (e.g., expanding or reducing the arch width) at a final stage in the treatment planning. In another example, the dental professional can modify, rotate, or move an individual tooth or a plurality of teeth, and the new arch width can be calculated based on the input from the dental professional.

At an operation 308, the treatment plan can be updated to incorporate the arch width modifications from operation 306. In one implementation, the modified arch width can be incorporated by optional treatment modeling engine 168 into the overall treatment plan for the patient. The treatment plan can be updated and each stage, including the arch width at that stage, can be displayed to the dental professional.

Figures 4A, 4B:
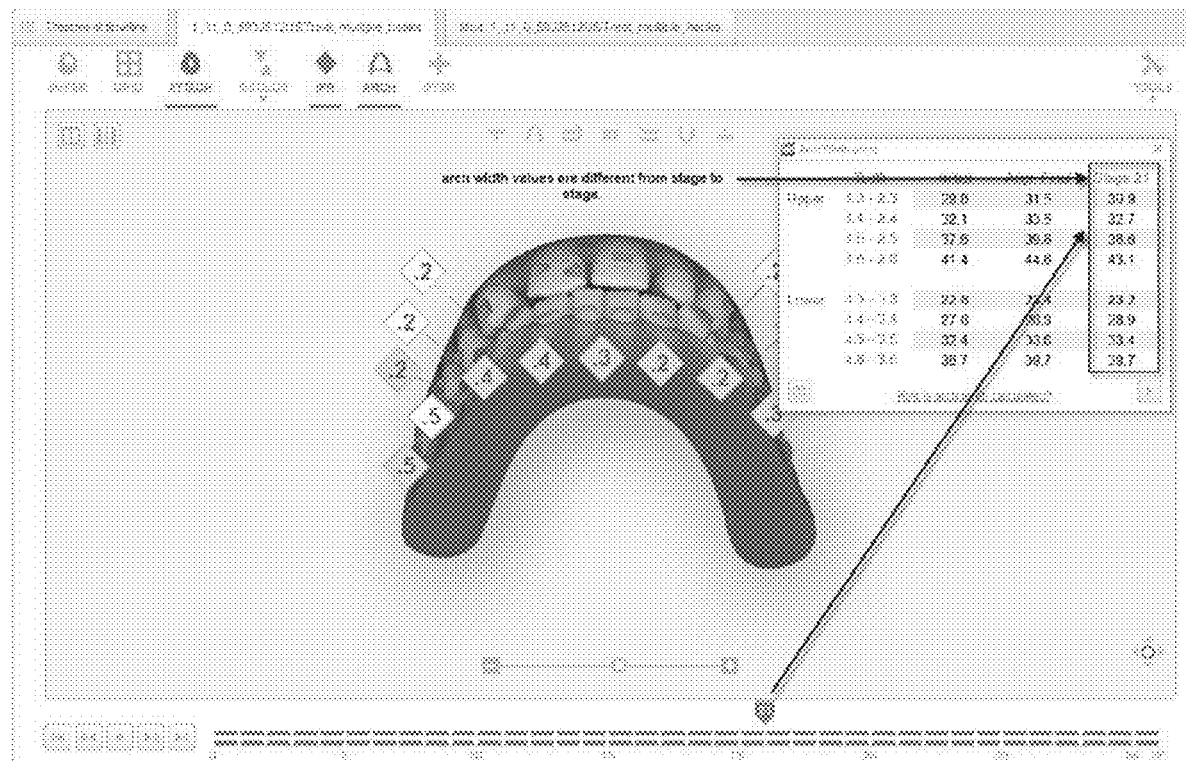
FIGS. 4A and 4B illustrate an example display of a patient's dental arch including the various arch widths between opposing teeth.

FIGS. 4A-4B illustrate an example display of a patient's dental arch including the various arch widths between opposing teeth. The dental professional can select which stage of the treatment to review, and the arch widths at that stage will be displayed. Additionally, as shown in FIG. 4B, arch width between opposing teeth can be shown for the initial, final, and selected stages (stage 21 is selected in the illustration). This gives the dental professional the ability to evaluate how the dental arch width changes over the course of treatment and to make adjustments to the arch width if necessary.

Figure 5A:
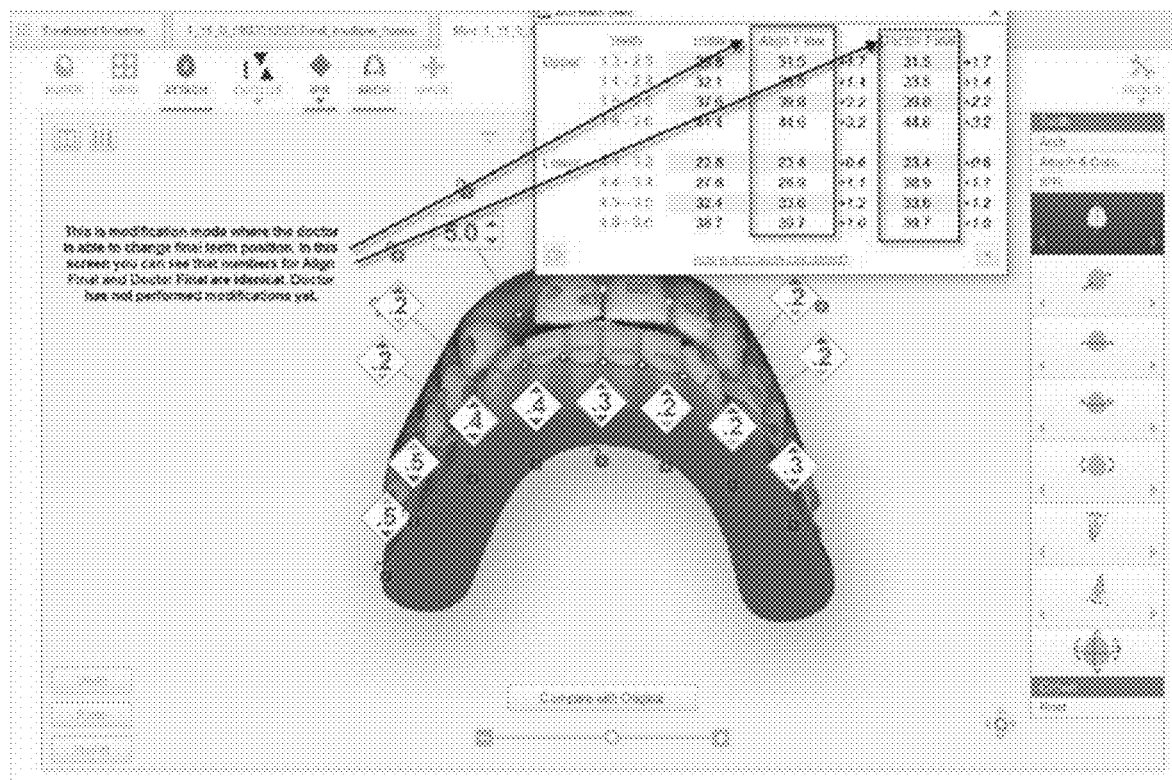
FIGS. 5A and 5B illustrate an example of a dental professional modifying an arch width of a patient's dental arch.
Figure 5B:
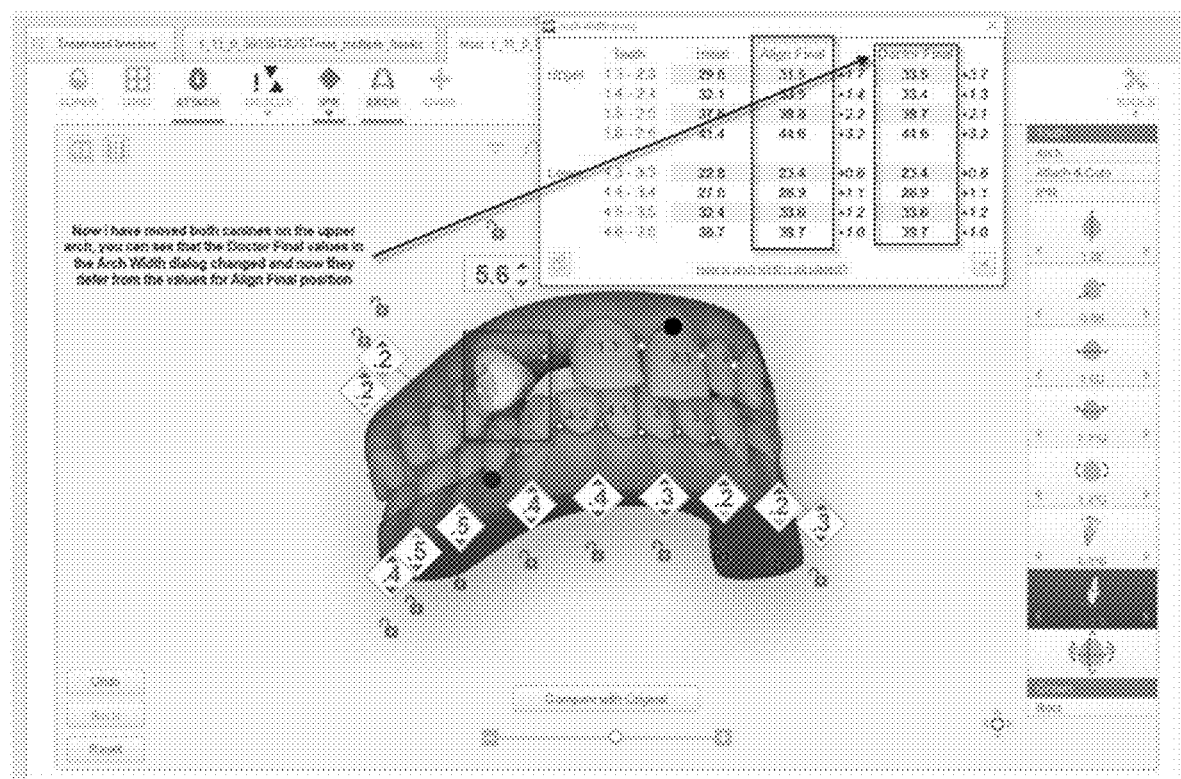

FIGS. 5A-5B illustrate an example of a dental professional modifying an arch width of a patient's dental arch. The dental professional is able to view the initial and final arch widths, and apply changes to the final arch width if necessary. In FIG. 5A, the dental professional has not yet performed an arch width modification. However, in FIG. 5B, the dental professional has modified the position of the canines in the upper arch, and the "Doctor Final" arch width has been updated to reflect the modification by the dental professional. In some implementations, the dental professional can modify the position and/or orientation of individual teeth, and the resulting arch width change can be reflected. In other implementations, the dental professional can input a desired arch width for a particular set of opposing teeth, and the teeth can be moved automatically by the system to reflect the modified width.

Figures 7, 8:
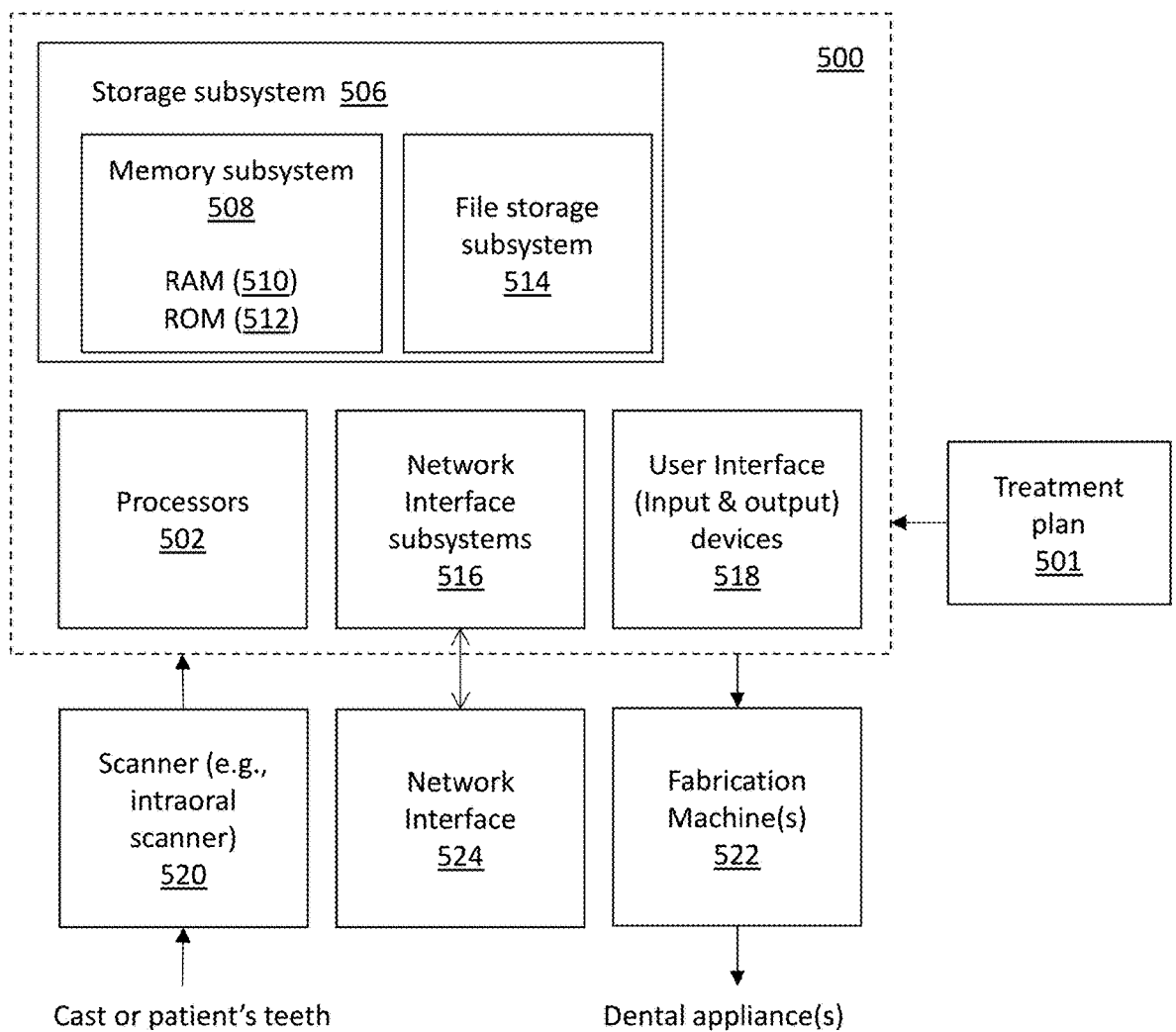
FIG. 7 is a simplified block diagram of a data processing system that may perform the methods described herein.
FIG. 8 illustrates one example of a display (shown as a table) showing arch widths.

The methods described herein may be performed by an apparatus, such as a data processing system, which may include hardware, software, and/or firmware for performing many of these steps described above. For example, FIG. 7 is a simplified block diagram of a data processing system 500. Data processing system 500 typically includes at least one processor 502 which communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 506 maintains the basic programming and data constructs that provide the functionality of the present invention. The software modules discussed above are typically stored in storage subsystem 506. Storage subsystem 506 typically comprises memory subsystem 508 and file storage subsystem 514.

Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system).

File storage subsystem 514 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 520 is responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524.

Fabrication machine 522 fabricates dental appliances based on intermediate and final data set information received from data processing system 500. In a distributed environment, fabrication machine 522 may be located at a remote location and receive data set information from data processing system 500 over network interface 524.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Thus, any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

EXAMPLES

The methods and system described herein may include user interfaces (e.g., displays, etc.) that may include one or more (or comparisons between multiple) arch width measurements. In some variations, the arch width measurements may be displayed on a 3D model (e.g., on a 2D image of a 3D model) of a patient's teeth, or a modified version of a patient's teeth. Alternatively or additionally, the arch width measurements may be displayed as a table. The table may reflect the inter-arch width between pairs of teeth on opposite sides of the upper or lower dental arch, such as between the canines, between the first premolars or first primary molars, between the second premolars or second primary molars, and/or between the permanent first molars.

The arch width may be measured from a point or region of the occlusal surface of each tooth where the long axis of the tooth intersects with the occlusal surface. The arch width may be measured linearly between both occlusal points for each pair of teeth. Measuring the arch width in this manner (e.g., from the points of intersection between the occlusal surface and the long axis of each tooth) may be advantageous, as it may provide a robust and consistent measurement across different patients. It may also provide a robust indicator of tooth movement accurately reflecting arch width. Although measuring arch width from the intersection of the occlusal surface and the long axis may be of particular user, other locations on the teeth may alternatively be used, including those discussed above.

FIG. 8 illustrates one example of a display (e.g., user interface display) showing arch widths (in mm) for a patient. In FIG. 8, the arch widths are shown between four pairs of upper teeth (URC-ULC, URD-ULD, URE-ULE, and UR6-UL6) and four pairs of lower teeth (LRC-LLC, LRD-LLD, LRE-LLE, and LR6-LL6). These eight arch width measurements are shown compared between a patient's initial tooth position ("initial") 805, a proposed modified final position ("Align final" 807), and a user-modified final position ("Doctor's final" 809). In some variations, additional modified arch arrangements may be compared. The number of arch widths (pairs of teeth) may also be varied; for example, a single upper and/or a single lower may be show, two pairs (from upper, lower or both arches), three pairs (from any combination of upper, lower or both), four pairs (from any combination of upper, lower or both), five pairs (from any combination of upper, lower or both), six pairs (from any combination of upper, lower or both), seven pairs (from any combination of upper, lower or both), eight pairs (from any combination of upper, lower or both), etc.

In this example, the arch width table reflects the inter-arch width between canines, first premolars or first primary molars, second premolars or second primary molars, and permanent first molars. As described herein, the inter-arch width may be measured from the point on the occlusal surface of each tooth where the long axis of said tooth intersects with the occlusal surface. The inter-arch width may be measured linearly between both occlusal points for each pair of teeth. In the some variations, e.g., as part of a tooth movement table (e.g., showing tooth movement during treatment or predicted for treatment), the crown movements of each tooth may be measured on the crown center and not on the occlusal projection of the long axis of the tooth; therefore, the sum of the crown movement of any pair of teeth may not be the same as change in inter-arch width for the same pair as shown in an arch width table such as shown in FIG. 8.

Figure 9:
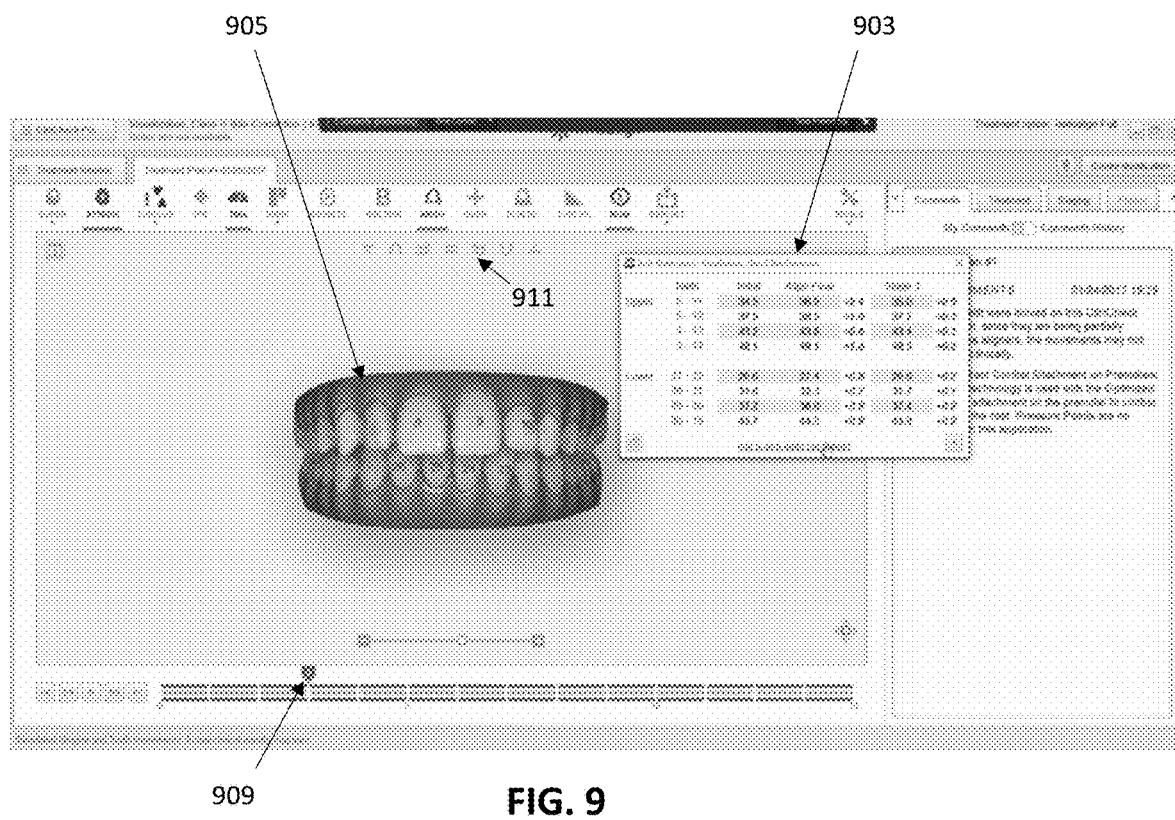
FIG. 9 illustrates one example of a display showing a patient's dentition (upper and lower arch) at a third stage of a dental treatment plan, further showing dental arch measurements between canines (6-11), first premolars (5-12), second premolars (4-13) and permanent first molars (3-14) for the initial tooth position, the final proposed tooth position and the displayed third stage of the treatment plan.

In some variations a differences between the different arch configurations (initial, user-modified final, etc.) may be displayed, as shown in FIG. 9. In FIG. 9, the user interface includes a display showing a patient's dentition (upper and lower arch), with a window showing arch widths measured between pairs of teeth (from the canines back to the molars) positioned on top/adjacent to the 3D image of the patient's dentition. In general, this window display 903 (e.g., the display of the arch widths) may be moved relative to the display of the 3D model 905. The model of the patient's teeth may be manipulated, e.g., using one or more tools 911 on the graphical user interface. These tools may allow rotation of the dental arches, tilting, zooming in/out, switching between fixed views (frontal, left side, right side, etc.) and/or removing one or the other dental arch (e.g., isolating the upper or lower dental arch), etc. The display in FIG. 9 also shows the estimated tooth numbering on each tooth.

In FIG. 9, the user may review a dental treatment plan by switching/toggling the display to illustrate the configuration of the patient's dentition at each stage in the treatment plan. In this example, the treatment plan includes 14 stages, and the user may move a slider 909 to switch the display between each stage. As the user changes the displayed modified view (e.g., corresponding to each stage of the treatment plan) the window showing the arch widths may dynamically (e.g., in real time or near real-time) update to reflect the arch widths for the various pairs of teeth and the comparison between the final stage and/or the current stage selected compared to the patient's initial dental arch configuration.

Figure 10A:
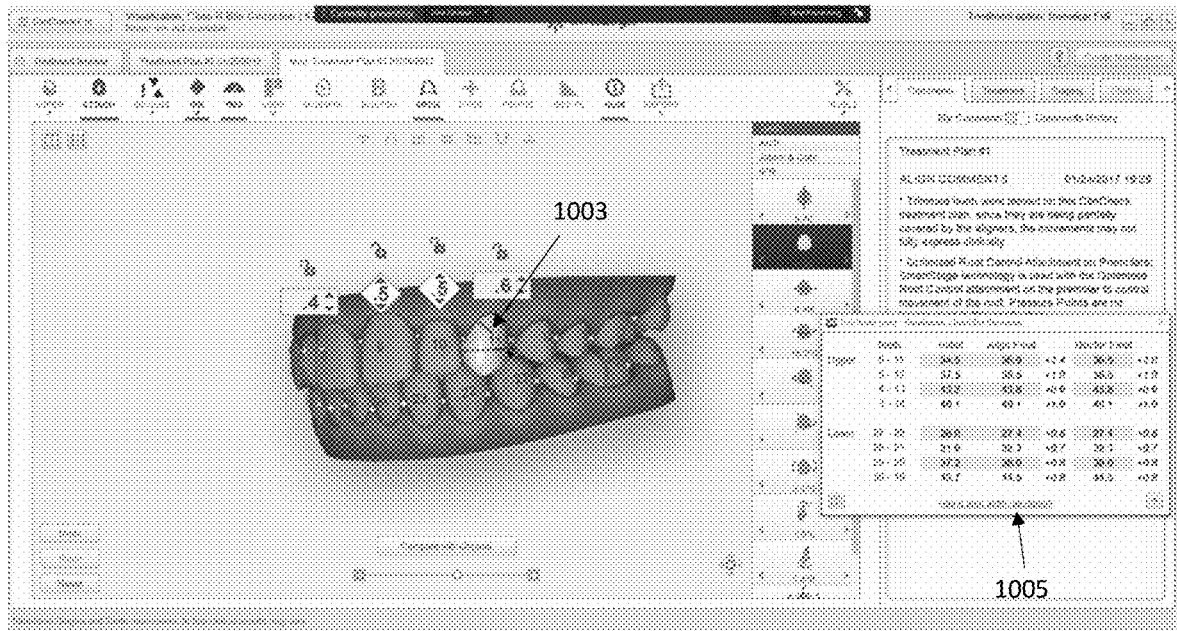
FIG. 10A shows one example of a display showing a 3D model of a patient's dentition with user interface tools for manipulating the 3D model, as well as a table showing dental arch measurements comparing the patient's initial tooth position, a proposed tooth position, and a position that may be modified by the user, e.g., by moving one or more teeth using the provided tools.
Figure 10B:
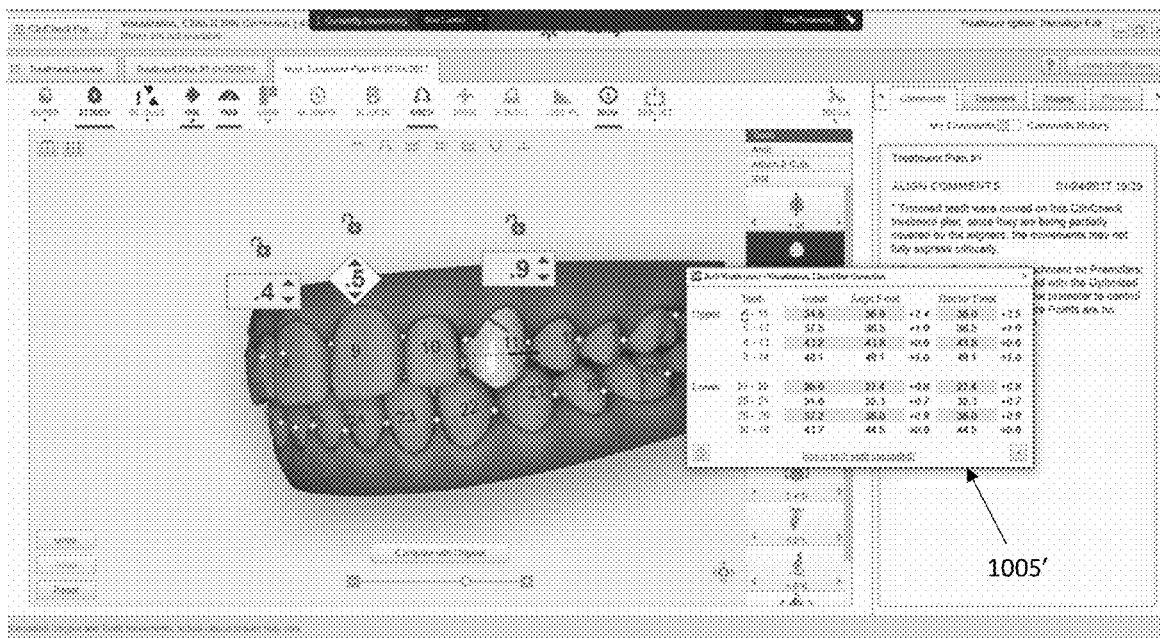
FIG. 10B shows the update to the dental arch measurements following manipulation of the 3D model by moving one of the canines (tooth 11).

In any of these variations, the teeth of the 3D model may be individually or collectively (in groups of selected numbers of teeth) moved or adjusted by the user. For example, tools may be provided to allow the user to manipulate the 3D model of the teeth from a particular proposed treatment stage (as shown in FIG. 9) or from the initial position of the teeth. In this case, the display may be interactive, allowing the user to adjust the position of the teeth using one or more tools and the arch width display may be adjusted in real time, as shown in FIGS. 10A-10B. In FIG. 10A, the upper and lower arches are shown and the user has selected on tooth (canine, tooth 11) 1003 to be moved. In FIG. 10A, the tooth is in an initial position, as yet unmoved. The arch width display window 1005, shows initial values for the arch widths of each of the initial arch, the proposed modified final ("align final") column, and the user-modified final column ("Doctor final") for all of the pairs of teeth shown. As the user moves the tooth, the arch width changes, as is apparent in the table 1005' in FIG. 10B, showing that the movement has enlarged the arch width, particularly between the canines (from 36.5 to 38.0 mm). In general, changes in the arch width due to user modifications may be displayed in real time or semi-real time and updated in the display.

In of the methods and systems described herein, the arch width measurements may be saved, transmitted, and/or stored. For example in some variations, the arch width measurements, including in some variations a table of arch width measurements, may be saved as a spreadsheet for later use or comparison. For example, the user interface may include an export function for exporting the arch width information (e.g., in a file format for later review).

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and/or methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc.

Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the patient matter may be practiced. As mentioned, other embodiments may be utilized and derived there from, such that structural and logical substitutions and changes may be made without departing from the scope of this disclosure. Such embodiments of the inventive patient matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer-implemented method comprising:
   identifying a first portion of a three-dimensional (3D) model of a patient's dentition corresponding to a first target tooth, the first portion of the 3D model of the patient's dentition being associated with one or more attributes of the first target tooth;
   identifying a second portion of the 3D model of the patient's dentition corresponding to a second target tooth opposing the first target tooth, wherein the second portion of the 3D model of the patient's dentition is associated with one or more attributes of the second target tooth;
   automatically measuring an arch width using the one or more attributes of the first target tooth the one or more attributes of the second target tooth, and patient information associated with the patient; and
   overlaying a graphic representing the arch width on a representation of the patient's dentition.

2. The computer-implemented method of claim 1, further comprising one or more of: taking the 3D model of the patient's dentition, receiving the 3D model of the patient's dentition from an intraoral scanner, and receiving the 3D model from a scan of a mold of the patient's dentition.

3. The computer-implemented method of claim 1, wherein the first target tooth comprises a tooth selected from the group consisting of canine, first bicuspid, first primary molar, second bicuspid, second primary molar, and permanent first molar.

4. The computer-implemented method of claim 1, wherein automatically measuring the arch width is based, at least in part on patient information including one or more of: patient age, eruption status, or patient gender.

5. The computer-implemented method of claim 1, further comprising outputting a modified version of the 3D model of the patient's dentition to include the arch width.

6. The computer-implemented method of claim 1, further comprising utilizing the arch width as part of an orthodontic treatment plan for the patient's dentition.

7. The computer-implemented method of claim 1, wherein identifying the portion of the 3D model is part of an operation of segmenting the 3D model of the patient's dentition.

8. The computer-implemented method of claim 1, wherein an attribute of the first target tooth comprises an intersection between an occlusal surface of the first target tooth and a long axis of the first target tooth.

9. The computer-implemented method of claim 1, wherein an attribute of the first target tooth comprises a lingual edge of the first target tooth.

10. The computer-implemented method of claim 1, wherein an attribute of the first target tooth comprises a buccal edge of the first target tooth.

11. The computer-implemented method of claim 1, further comprising, after automatically measuring the arch width:
    receiving an input that adjusts a position or rotation of the first target tooth; and
    repeating measuring the arch width between the one or more attributes of the first target tooth and the one or more attributes of an opposing tooth.

12. The computer-implemented method of claim 1, wherein the patient information is used, at least in part, to determine which teeth to use to calculate arch width.

13. The computer-implemented method of claim 1, wherein automatically measuring the arch width comprises determining which teeth to use to calculate arch width based on the patient's age.

14. A computer-implemented method comprising:
    accessing a three-dimensional (3D) model of a patient's dentition;
    identifying a first portion of the 3D model of the patient's dentition corresponding to a first target tooth, the first portion of the 3D model of the patient's dentition being associated with one or more attributes of the first target tooth;
    identifying a second portion of the 3D model of the patient's dentition corresponding to a second target tooth opposing the first target tooth, wherein the second portion of the 3D model of the patient's dentition is associated with one or more attributes of the second target tooth;

automatically measuring an arch width using the one or more attributes of the first target tooth, the one or more attributes of the second target tooth, and patient information associated with the patient, wherein the patient information is used, at least in part, to determine which teeth to use to calculate arch width; and overlaying a graphic representing the arch width on a representation of the patient's dentition.

* * * * *